United States Patent
Mundheim

(10) Patent No.: US 9,249,021 B2
(45) Date of Patent: Feb. 2, 2016

(54) CRYSTALLIZATION OF POLY AMMONIUM PHOSPHATE IN PARTICULAR ORGANIC MATERIAL AND USES THEREOF

(76) Inventor: Atle Mundheim, Omastrand (NO)

( * ) Notice: Subject to any disclaimer, the term of this patent is extended or adjusted under 35 U.S.C. 154(b) by 0 days.

(21) Appl. No.: 13/265,844

(22) PCT Filed: Apr. 21, 2010

(86) PCT No.: PCT/NO2010/000145
§ 371 (c)(1),
(2), (4) Date: Mar. 4, 2012

(87) PCT Pub. No.: WO2010/123376
PCT Pub. Date: Oct. 28, 2010

(65) Prior Publication Data
US 2012/0171299 A1    Jul. 5, 2012

(30) Foreign Application Priority Data

Apr. 21, 2009   (NO) .................................. 20091555

(51) Int. Cl.
| | |
|---|---|
| *A01N 25/08* | (2006.01) |
| *C01B 25/28* | (2006.01) |
| *A01N 59/26* | (2006.01) |
| *C01B 25/40* | (2006.01) |
| *C05B 13/06* | (2006.01) |
| *C05G 3/00* | (2006.01) |
| *C05G 3/02* | (2006.01) |
| *C09K 21/04* | (2006.01) |

(52) U.S. Cl.
CPC ................ *C01B 25/28* (2013.01); *A01N 59/26* (2013.01); *C01B 25/405* (2013.01); *C05B 13/06* (2013.01); *C05G 3/0041* (2013.01); *C05G 3/02* (2013.01); *C09K 21/04* (2013.01)

(58) Field of Classification Search
None
See application file for complete search history.

(56) References Cited

U.S. PATENT DOCUMENTS

| | | | |
|---|---|---|---|
| 2,935,471 A | 5/1960 | Aarons | |
| 3,398,019 A | 8/1968 | Langguth et al. | |
| 5,213,783 A * | 5/1993 | Fukumura et al. | ............. 423/305 |
| 6,107,242 A | 8/2000 | Ackerman et al. | |
| 2008/0054230 A1 * | 3/2008 | Mabey et al. | ................. 252/606 |
| 2008/0121461 A1 | 5/2008 | Gross et al. | |
| 2009/0217723 A1 * | 9/2009 | Sanders | ............................ 71/11 |

OTHER PUBLICATIONS

Bagarinao, T. and Lantin-Olaguer, I., From triphenyltins to integrated management of the "pest" snail Cerithidea cingulata in mangrove-derived milkfish ponds in the Philippines, Hydrobiologia 437: 1-16, 2000.
Written Opinion of the International Preliminary Examining Authority, related to PCT/NO2010/000145, issued on Jul. 29, 2011.
Norwegian office action of the priority Norwegian application, Application No. 20091555, issued on Oct. 20, 2009.
Extended European Search Report for counterpart European Application No. EP 10767355.0-1454/2421374, issued on Dec. 3, 2014.

* cited by examiner

*Primary Examiner* — Robert A Wax
*Assistant Examiner* — Melissa Mercier
(74) *Attorney, Agent, or Firm* — Zareefa B. Flener; Flener IP Law, LLC

(57) ABSTRACT

An organic particular material and a method for producing the material is disclosed, as well as multiple uses of the material produced by the same method for use as soil improver, combating the Iberia snail, fire resisting absorption of flammable liquids as well as fire extinguisher.

7 Claims, No Drawings

CRYSTALLIZATION OF POLY AMMONIUM PHOSPHATE IN PARTICULAR ORGANIC MATERIAL AND USES THEREOF

The present invention concerns a compound material for combating the Iberian snail, while the material simultaneously works as a slow working fertilizer and soil improver where nutritional salts do not leak to groundwater, water courses, lakes or the sea, as evident from the introduction to the following claim 1.

More specifically, the invention concerns an organic material where a certain composition of water in liquid form, ammoniac, phosphoric acid and diammonium phosphate is brought to crystallization in the organic material so that this is impregnated in fibers and on surfaces with crystallized poly ammonium phosphate with very long chain lengths so that the crystals have very low water-solubility, while also being slow to convert to nitrogen for bacteria.

The invention also concerns a method for producing the complex material where a specific liquid solution of water, ammonia, phosphoric acid and diammonium phosphate is reacted, whereupon the mixture is applied to the organic material or the organic material is mixed into the solution, after which the organic material soaked in the solution is dried so that water evaporates, whereby crystallization of the poly ammonium phosphate with very long chain lengths takes place in the organic material.

The invention also concerns a method for further making the organic material infused with the specific liquid solution of water, ammoniac, phosphoric acid and diammonium phosphate less exposed to leaking nutrient salts to groundwater, water courses, lakes and the sea when used.

The invention also concerns using the compound material to kill the Iberian snail, as well as a use for preventing the Iberian snail from residing in or entering an area, as well as a use for preventing the Iberian snail from being spread through transportation and commerce of plants from garden centers and plant and soil manufacturers.

The invention also concerns a utilization of the material as a fertilizing soil improving material, where leakage of fertilizer to ground water, water courses, lakes and the sea is eliminated, while at the same time the fertilizer departs from its organic host slowly, reducing the frequency of fertilization.

The invention also concerns a utilization of the organic impregnated material as fire-resistant oil absorbent and/or fire extinguishing material.

The invention relates to the technology that has to do with producing a material in an organic host which kills the Iberian snail, prevents the Iberian snail from reproducing and spreading, while simultaneously functioning as a fertilizer and soil improver which may be used in nature and as fertilizer in plant soil, gardens, fields and cultivated areas.

The invention also relates to the technology that has to do with producing a fertilizer with long lasting effects from slow release of nutrients, while the nutrients do not leak to ground water, water courses, lakes or the sea.

The invention also concerns utilizations of the material.
Well-Known Methods in Use Today There is currently no effective way of preventing the Iberian snail from spreading or causing damage. This snail causes a lot of damage on the crops and gardens it spreads to. It mainly spreads through the commerce of plants/plant soil where eggs are hatched into snails and escape into nature. The snail reproduces at a staggering pace, and surpasses and kills its congeners. It lays eggs which survive winter underground, after which newly hatched snails go up to the surface in the spring.

This problem is considered a large threat to agriculture and to garden owners globally, with the exception of polar areas. One known treatment that reduces the Iberian snail population is the use of nematodes, which are living organisms that attack the snails biologically and causes them to stop ingesting nourishment.

Today, there are materials one can disperse on the soil which consist of iron (III) phosphate as active ingredient mixed with a material in the form of granulate which the Iberian snail eats. After ingesting this, the snail dies from having stopped ingesting nourishment.

Furthermore, is it known that the current practice, with the means that are known, is that the Iberian snail must be picked up and physically killed, according to the best present recommended method for limiting damages.

It is known that peat moss is a good element in soil improving materials, and a number of mixtures where peat moss is an ingredient are used as plant soil, flower soil or dispersed on the ground.

It is known that fertilizers which with the help of bacteria influence convert ammonium into nitrogen are very efficient as fertilizer, and several products are on the market. Some of these have the ability to work over time, with the least amount of leakage as a result of influence from water.

It is further known that poly ammonium phosphate with long chain lengths over 50-100 have very low solubility in water, and that this solubility decreases the longer the chain lengths are.

It is further known that conversion of ammonium into nitrogen only takes place by bacteriological activity when poly ammonium is present, dissolved in water.

The limitation of today's methods is that they only limit the number of Iberian snails for a short period. Each snail lays up to 400 eggs in the fall, and these winter in the earth and surface in the spring.

Nematodes have limiting criteria for application, and only work within a narrow temperature area, and then with given conditions for moisture. Among other things, the lawn must be watered well before and after treatment. The lawn cannot become dry during the first two weeks following treatment. Because nematodes are living organisms, the package must be stored unopened in a refrigerator at 5° C. until it is used. The nematodes cannot withstand frost. The nematodes are sensitive to light; the treatment must take place during the evening or during cloudy weather.

Iron (III) phosphate contains 10 g/l active ingredient and it is only permitted to be used 4 times per season in a concentration of 5 gram/m$^2$. Any more than this is harmful to nature.

None of the known products for combating the Iberian snail have fertilizing and soil improving effects on gardens, beds, fields and cultivated areas.

None of the known products can be used as slow working fertilizer in soil for potted plants and plant soil that is transported so that spreading of eggs and snails can be avoided in transportation and sale, which incidentally is the manner in which the Iberian snail is geographically spread.

It is known from U.S. Pat. No. 6,107,242 that particular crystallized poly ammonium phosphate or super phosphate can be brought to attach to the pores of crushed coconut shell. The powder has a preferred particle size of 1 μm, and this is specifically dissolved with water spray during the application process, while this is simultaneously crushed into the coconut shell when this is crushed in a so-called "hammer mill." 4 g is typically applied to 8 g super phosphate and 65 ml water to each liter crushed coconut shell powder, and where specifically the crystals in the process, with the help of mechanical force, should penetrate the organic fibers.

It is an aim of the invention to produce a new and improved composite material for combating Iberian snails, as well as to produce in addition to the compound material a soil improving material with slow fertilizing effect from which nutrient salts do not leak to water systems, lakes or the sea.

It is furthermore an aim of the invention to produce an organic material wherein a liquid is brought to crystallize into polymeric poly ammonium phosphate in the organic material where polymeric poly ammonium phosphate has chain lengths in a size order that causes them to have very low solubility in water.

It is furthermore an aim of the invention to produce a method for the production of the compound material.

It is furthermore an aim of the invention to produce a method for making the crystallized polymeric poly ammonium phosphate of the organic material less vulnerable to leak nutrient salts to ground water, water systems, lakes and the sea than it already is due to its long chain lengths and thereby minimal solubility in water.

It is furthermore an aim of the invention to produce a use for the compound material for killing Iberian snails, as well as a use for preventing the Iberian snail from residing in or entering an area, as well as a use for preventing the Iberian snail from spreading through transportation and commerce of plants from garden centers and plant and plant soil manufacturers.

It is furthermore an aim of the invention to produce a use of the compound material as fertilizing soil improver, where leakage of fertilizer to ground water, water systems, lakes and the sea is eliminated, while the fertilizer leaves its organic host slowly, reducing the fertilizing frequency.

It is furthermore an aim of the invention to produce a use for the compound material as fire-resistant oil absorbent and/or fire extinguisher.

The methods, utilizations, according to the invention are characterized by the features evident from the characterization in the following independent claims.

Further features of the invention are specified in the dependent claims.

According to the present invention there has thereby been produced a new compound material well-suited for combating Iberian snails, as well as producing with the same compound material a soil improving material with slow working fertilizing effect from which nutrient salts do not leak to water systems, lakes or the sea.

Furthermore, according to the present invention there has been produced an organic material wherein a liquid is brought to crystallize into polymeric poly ammonium phosphate in the organic material where polymeric poly ammonium phosphate has chain lengths in a size order which gives it very low solubility in water.

Furthermore, according to the present invention there has been produced a method for producing the compound material.

According to the present invention there has been produced a method for making the crystallized polymeric poly ammonium phosphate of the organic material less vulnerable to leak nutrient salts to ground water, water systems, lakes and the sea than it already is due to its long chain length and thereby minimal water solubility. According to the present invention there has been produced a use of the compound material for killing the Iberian snail, as well as a use for preventing the Iberian snail from residing in or entering an area, as well as a use for preventing the Iberian snail from spreading through transportation and commerce of plants from garden centers and plant and plant soil producers.

According to the present invention there has been produced a use of the compound material as fertilizing soil improver, where leakage of fertilizer to ground water, water systems, lakes and the sea is eliminated, while the fertilizer leaves its organic host slowly, reducing the fertilizing frequency.

According to the present invention there has been produced a use of the compound material as a fire-resistant oil absorbent and/or extinguisher.

The invention is characterized by a liquid absorbing and slowly degradable organic particular material, preferably peat moss which is also known under the term "Pcat", dry or partially hydrous, being brought to contact with a liquid produced from water, ammonium, phosphoric acid, and diammonium phosphate.

The invention is characterized by the liquid being produced by homogenous mixing of the elements of the liquid in this exact order;
a) Water is mixed with ammonium.
b) Water/ammonium is mixed with phosphoric acid.
c) Water/ammonium/phosphoric acid is mixed with diammonium phosphate.

The invention is characterized by the liquid being produced with the preferred exact reciprocal proportion of ingredients given by;

| | |
|---|---|
| a) Water | 1843 kg |
| b) Ammoniac 25% | 630 kg |
| c) Phosphoric acid 75% | 542 kg |
| d) Diammonium phosphate | 673 kg | where other amounts may be mixed as long as the exact reciprocal proportion of the ingredients is kept constant.

The invention is further characterized by the ready-made reacted liquid having a pH of 8+/−0.5%, and a phosphate content (P) of 9%+/−0.5%, and an ammonium content (N) of 8%+/−0.5%.

The invention is characterized by bringing the prepared liquid into contact with a liquid absorbing particular organic material, preferably peat moss/peat, where the material/peat moss/peat is dry or partially hydrous, by applying the liquid to the organic material or by mixing the material in the liquid whereby in both cases parts of, or all, the liquid permeates the organic material/peat moss.

The invention is further characterized by the option of spraying the liquid of water, ammoniac, phosphoric acid and diammonium phosphate on already dried organic material, or soaking dry organic material in the already produced liquid of water, ammoniac, phosphoric acid and diammonium phosphate, or soaking organic material containing water, as peat moss often contains 50% water, in the already produced liquid of water, ammoniac, phosphoric acid and diammonium phosphate in a process where the concentration of liquid in the mixing tub is maintained by steady new infusion of concentrated liquid.

The invention is characterized by the particular organic material/peat moss with liquid of homogenously mixed and reacted water, ammoniac, phosphoric acid and diammonium phosphate absorbed, being dried so that water evaporates and crystallization of polymeric poly ammonium phosphate thereby takes place in the particular organic material/peat moss.

The invention is further characterized by the polymeric poly ammonium phosphate (NH4PO3)n

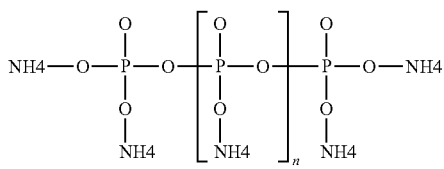

as a result of the exact order of the mixing of ingredients in the liquid, as well as the exact reciprocal proportion of the ingredients in the liquid, crystallizing into relatively water-insoluble polymeric poly ammonium phosphate with chain length n=50-20000 inside the fibers, in and on, the organic material/peat/peat moss with evaporation of the water present in the liquid.

The invention is further characterized by such drying taking place at temperatures from surrounding temperature up to approximately 170° C., but not much higher as temperatures above this lead to decomposition and ammoniac degasification of the crystallized polymeric poly ammonium phosphate that is crystallized during the drying of the fiber of the organic material.

The invention is further characterized by having a preferred drying temperature of over 100° C. as one then additionally achieves making peat/peat moss hydrophobic and thereby further prolonging the lifespan of the active crystallized polymeric poly ammonium phosphate of the fibers by exposing it to less water when placed in nature. At the same time, such drying will make peat/peat moss oleophilic, and suitable as fire-resistant oil absorbent, and further suitable as extinguisher and as an addition in fire extinguishing water as a result of water-insoluble crystallized poly ammonium phosphate in the fibers of the organic particular material.

Advantages of the present new method.

The present invention distinguishes itself from existing methods/inventions because long-chained poly ammonium crystals are produced in an organic host using the same method, from water evaporating from a specific measured and mixed liquid mixture of water, ammoniac, phosphoric acid and diammonium phosphate which causes practically all crystals to form in the organic material where they function as a very slowly dissolving nutrient salt if used as soil improver; if applied to Iberian snails or areas where these exist, kills these or prevents them from residing in the area; or, if used as absorbent, functions as a flame retardant; or, if used on fire, extinguishes.

The present invention distinguishes itself from existing methods/inventions in that when it is used as soil improver/fertilizer it will not leak to lakes, water or water systems.

The present invention distinguishes itself from existing methods/inventions in that when it is used as prevention against Iberia snail it does not have any toxic impact at nature. Furthermore it distinguishes itself in that it can be incorporated as natural fertilizer for greenhouse plants and thereby stop hatching and spreading of eggs from Iberia snail.

Furthermore it distinguishes itself in that it can be used as a barrier surrounding cultivated areas to prevent Iberia snail to invade the cultivated areas.

The present invention distinguishes itself from existing methods/inventions in that the organic material with crystallized poly ammonium phosphate has multiple uses such as fire-resistant oil absorbent, as well as extinguisher.

The present invention is characterized by bringing organic particular material, preferably peat/peat moss, into contact with a liquid made from water, ammoniac, phosphoric acid and diammonium phosphate in the order mentioned, where the liquid mixture is determined precisely from the preferred proportions 49.85 weight % water, 17.13 weight % ammoniac (counted from 35% concentration), 14.73 weight percent phosphate acid (counted from 75% concentration) and 18.29 weight % diammonium phosphate.

The present invention is further characterized by the liquid mixture being brought to crystallization in the particular organic material from evaporation of water from the liquid in the material.

The present invention is further characterized by having multiple uses for the material.

The invention shall be explained closer in the following examples, wherein:

EXAMPLE 1

36.79 kg solution was made from 18.43 kg water wherein 6.3 kg 25% ammoniac was mixed, after which 5.42 kg 75% phosphoric acid was mixed in, and where at the end 6.73 kg diammonium phosphate was added. During preparation some ammonia gas developed, which was aired out. After preparation the liquid became a clear light yellow nearly odor-free liquid without turbidity. PH was 8.0, and analyses showed a phosphate content (P) of 9% and an ammonia content (N) of 8%.

EXAMPLE 2

1 liter peat moss with a water content of 50% was mixed with 1 liter of the liquid from example 1. After impregnation, the moss was extracted and a significant portion of the liquid was pressed out. The moss was then dried at approx. 50 degrees Celsius temperature. This was also repeated with 1 liter dried peat moss with a water content of 12%. After complete dehydration the respective materials with crystallized poly ammonium phosphate were soaked in water for 24 hours. Solid matter was then filtered off, and water was analyzed for N and P. The analyses showed only traces of N and P, and showed that water-insoluble poly ammonium phosphate was crystallized in the peat moss.

EXAMPLE 3

Larger sections of 1 m3 of already prepared peat moss was made and dried in accordance with the recipe described in examples 1 and 2. The product was dispersed in a section of a garden from which approximately 100 Iberian snails were picked every day. After application the Iberian snail disappeared from the area.

EXAMPLE 4

The product according to the invention was dispersed in a flower bed exposed to attacks from the Iberian snail. This was placed on a lawn where there were a lot of Iberian snails. After the application no Iberian snails entered the flower bed.

EXAMPLE 5

10 Iberian snails of different sizes were placed inside a circle that was surrounded by a 5 cm ring of the product. The snails did not cross the ring until dehydration forced them to cross. The smaller snails reached 10 cm past the ring before they died. The larger snails reached approximately 1 meter, while the largest ones slimed out of their own skin and carried on. However, after this it appeared that exposure to just a few grains of the product killed them immediately.

EXAMPLE 6

Eggs from the Iberian snail were placed in a flower pot with a mixture of the product in a closed container. No eggs were hatched.

EXAMPLE 7

A small amount of the product was dispersed on an unfertilized lawn on half of the surface of the lawn at late fall. Next spring the part of the lawn that had been exposed to the product showed a very pronounced grass growth, significantly quicker than the part that had not been exposed. The fertilizer had not leaked during a winter with much rainfall.

EXAMPLE 8

The product was compared with heat activated peat moss with consideration for oil absorbing abilities. It turned out that 1 liter of prepared moss absorbed 1 liter of oil, which was exactly the same as untreated moss.

EXAMPLE 9

Absorption test from test 8 was repeated with 1 liter untreated and 1 liter prepared moss, wherein 4 dl diesel oil was absorbed. Attempts were made to ignite the tests with a gas flame. Prepared moss would not ignite at all, while untreated moss burned very well and was easily ignited.

EXAMPLE 10

An oil drum with 5 liter waste oil was set on fire and given a chance to achieve a high temperature over time. 0.5 liter of prepared peat moss was slowly dispersed over the fire. The fire was immediately extinguished.

The invention claimed is:
1. A method for ameliorating the infestation of an area of soil or other plant growth media by snails, comprising the steps of,
    a) combining a particulate organic material with crystallized poly ammonium phosphate,
    b) identifying an area of soil or other plant growth media infested by, or at risk for infestation by snails,
    c) applying the organic material to the area, or in a perimeter around the area.
2. The method according to claim 1, wherein the snails are Iberian snails.
3. The method according to claim 1 or 2, wherein the organic material is combined with the crystallized poly ammonium phosphate by exposing the organic material to an aqueous solution comprising water, ammonia, phosphoric acid and diammonium phosphate, and thereafter drying the organic material until crystals of poly ammonium phosphate form.
4. The method according to claim 3 wherein the organic material is peat moss.
5. The method according to claim 3, wherein the solution is prepared by mixing together the following ingredients in the following amounts, or in amounts having the same relative percentages by weight:
    a) 1843 kg of water,
    b) 630 kg of 25% ammonia,
    c) 542 kg of 75% phosphoric acid, and
    d) 673 kg of diammonium phosphate.
6. The method according to claim 4, wherein the peat moss is dried at a temperature from room temperature to 170 degrees C.
7. The method according to claim 6, wherein the peat moss is dried at a temperature of from 100 degrees C. to 170 degrees C.

* * * * *